United States Patent [19]
Kothe

[11] Patent Number: 5,463,917
[45] Date of Patent: Nov. 7, 1995

[54] PROCESS FOR PRODUCING, IN PARTICULAR, TWO-PART SURGICAL INSTRUMENTS

[76] Inventor: Lutz Kothe, Bodmaner Str. 15, 78315 Radolfzell 14, Germany

[21] Appl. No.: 129,586

[22] Filed: Sep. 30, 1993

[30] Foreign Application Priority Data

Oct. 16, 1992 [DE] Germany .......................... 42 34 884.6

[51] Int. Cl.⁶ ................................. B26F 3/00; B26F 3/16; B23H 7/02; A61B 17/06
[52] U.S. Cl. ........................................ 76/119; 76/11; 83/16
[58] Field of Search ................ 76/101.1, 104.1, 76/119, 11; 219/70, 159; 83/171, 36, 16

[56] References Cited

U.S. PATENT DOCUMENTS 1,990,694  2/1935  Jacobs ................................ 76/104.1
3,442,159  5/1969  Sarvie ................................ 76/101.1
4,683,792  8/1987  Demont .................................. 83/16

FOREIGN PATENT DOCUMENTS 19195  of 1914  United Kingdom .................. 76/101.1

*Primary Examiner*—Douglas D. Watts
*Attorney, Agent, or Firm*—Bachman & LaPointe

[57] ABSTRACT

In the case of a process for producing, in particular, two-part surgical instruments, a blank is separated into two parts by means of cutting equipment. Contours are formed in the blank simultaneously during the separation by means of the cutting equipment.

4 Claims, 1 Drawing Sheet

PROCESS FOR PRODUCING, IN PARTICULAR, TWO-PART SURGICAL INSTRUMENTS

The invention concerns a process for producing, in particular, two-part surgical instruments, a blank being separated into two parts by means of cutting equipment, as well as a device for this.

Conventional two-part round instruments such as, for example, needle holders, jaws for endoscopic forceps, pincers, and many more, at the present time are produced from a blank, this blank being split axially by means of cutting equipment. After this, each part of the instrument is finished by itself, as a rule, machining processes being used here. These processes also are used to produce teeth in jaws and, in particular, also the closure for a two-part surgical instrument. The work here must be very precise since the closure is to fit together, respectively since the jaw parts should be made at least partially as mirror-inverted or symmetrical.

The task of the present invention is to simplify the production of surgical instruments significantly.

The fact that contours are made in the blanks by means of the cutting equipment during the separation leads to the solution of this task.

This means that contours which exactly agree, resp. match, are made in the blank, resp. in both parts of it, right during the separation process. In particular, this is true of the closure and also for the jaw parts, which no longer have to be refinished in the case of this type of processing.

The new processing technique invented which, in particular, also includes the possibility of turning the blank and/or the cutting equipment during the separation process, not only can determine external contours of the instrument before its division by means of separation or shaping true to size, but during the halving of the entire instrument, respectively of the corresponding parts, but also a large number of desired, and/or required graduations and recesses may be formed in the instrument parts at the same time. In this way a complete two-part instrument, which requires significantly less finishing, arises from only one blank, be it round or shaped differently.

Preferably, a wire eroding device is used as the cutting equipment. However, an appropriate laser, a water jet, or other known cutting instrument may be used as the cutting equipment. It is essential only that either the cutting equipment can change position with respect to the blank, or that the blank can change position with respect to the cutting equipment during the cutting process. As a rule, it should be the case here that the blank is turned on a turntable while the cutting equipment is moved along the blank in the cutting direction. However, other designs also are conceivable. Further, in particular, it is envisioned that several blanks be mounted on one turntable and processed together. This raises the efficiency of the process.

The process may be used on jaw parts for endoscopic forceps, resp. basically for all two-part symmetrical or mirror-inverted instruments or parts of instruments. Also individual instruments or parts, which on the basis of their nature and repeating shapes may be fitted together resp. be shaped mirror-inverted and/or into the previous form, may be produced advantageously with the process invented. However, this process primarily should find application for two-part instruments or instrument parts.

The use of the process in producing a closure of shears, forceps, or similar instruments, which consist of two parts which are connected together by means of a hinge, is particularly to be emphasized. For example, first the jaw is slit up to the beginning of the closure with a wire erosion device. Now the blank is turned by 90°, a slit running transverse to the longitudinal axis of the blank being made. Then the closure surface is cut along the longitudinal axis up to the end of the closure. Now there is a further rotation of the blank by a further 90°, so that again a slit transverse to the longitudinal axis of the blank is produced. Now the entire blank may be separated along its longitudinal axis.

An absolutely exact closure is produced by means of the process invented since both parts are completely identical in this area. Refinishing is no longer necessary.

During the turning of the blank corresponding inner edges in the area of the closure or also on other positions of the instrument may be rounded off very simply. The desired radius in this case may be chosen freely. On the one hand the danger that the parts will break is significantly reduced here, and on the other hand there is also an improved possibility for cleaning, since no dirt may collect in a corner.

For the device invented, the cutting equipment additionally should be equipped with a CNC- or other turntable and/or have a horizontal tightening capability if these features are not already present. For example, a multiple spindle round table may be used. The turntable may be coupled with the machine controls if possible, so that motions which are in agreement resp. dependent on one another are possible.

The process invented and the device may be used for many purposes. Since the wire erosion process is known in and of itself, however, patent protection is claimed for its use for producing surgical instruments.

Further advantages, features, and details of the device result from the following description of preferred specific embodiments as well as by means of the drawings; to wit FIG. 1 shows a schematic representation of a device made in accordance with the invention for producing a two-part surgical instrument, for example a needle holder;

Figure 1:
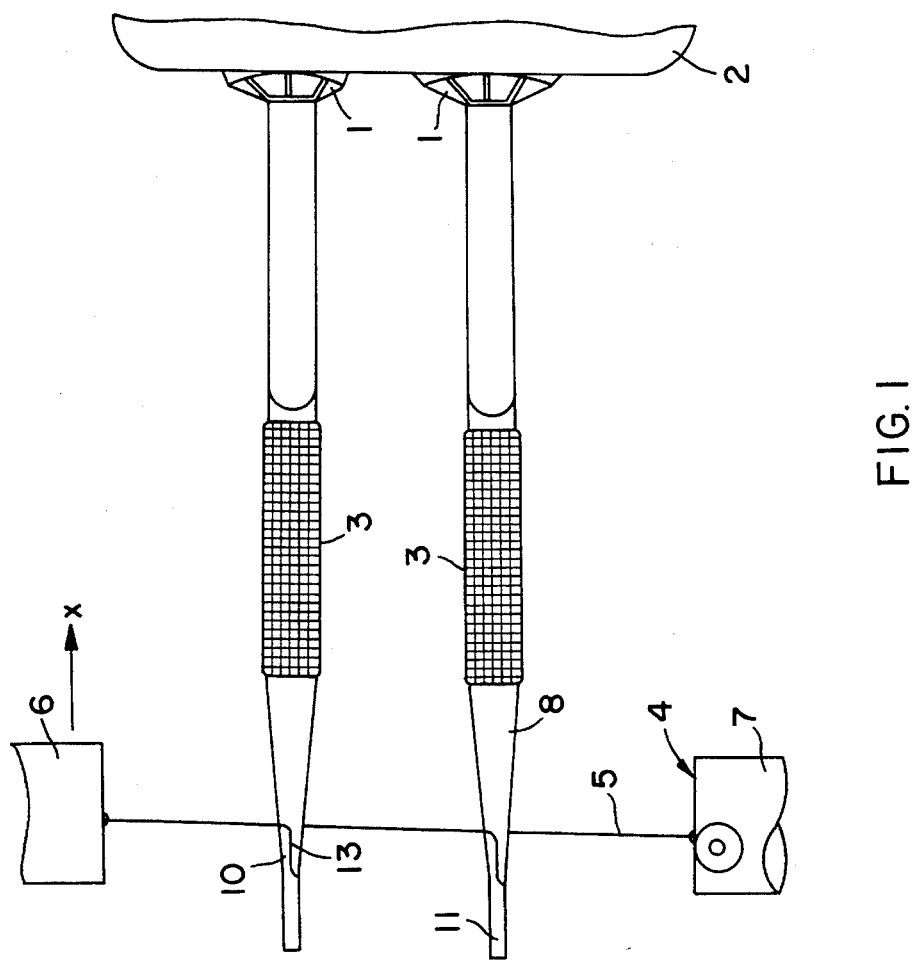

In accordance with FIG. 1, two blanks 3 for a surgical instrument, for example a needle holder, are fastened to collets 1 of a turntable 2. These blanks 3 may be turned by at least 180° by means of the turntable 2. The turntable 2, together with the blanks 3, is aligned with cutting equipment 4, which in the embodiment under consideration is made as a wire erosion device. In this case an eroding wire 5 runs from a wire feed 6 to a wire takeup 7. Cutting equipment of this type is known and therefore is not to be described in greater detail here.

The entire cutting equipment 4 is guided in the cutting direction x, cutting the blanks 3 in the desired amount and direction. Of course, it is also possible to have the cutting equipment 4 fastened in place and to guide the turntable 2 towards the cutting direction x.

The following process is carried out by means of this device invented:

In the specific embodiment under consideration, a blank 3 is a Barraquer needle holder. This is chucked into the collet 1. Then its external contours are produced by erosion. Of course, it is also possible that the external contours have been produced previously by means of another machining process or the like.

Figure 2:
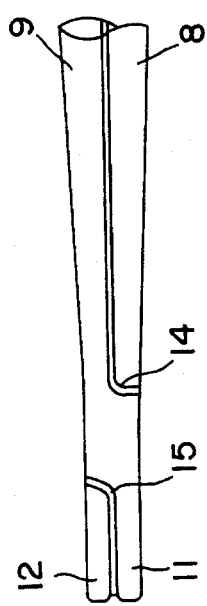
FIG. 2 shows a top view on a part of the needle holder in accordance with FIG. 1.
Figure 3:
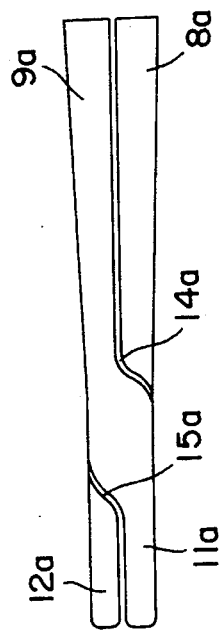
FIG. 3 shows a top view of a further embodiment of a part of a needle holder.

However, it is important that a needle holder have two approximately symmetrical or mirror-inverted forceps jaws 8 and 9 which in the area of the closure 10 are connected with one another, after the closure two mirror-inverted jaw parts 11 and 12 being made. For the rough production of these two mirror-inverted parts, the blank 3 is split from the jaw by means of the eroding wire 5, i.e. the eroding wire 5 is moved axially through the blank 3 precisely in the middle. This is performed up to the closure 10. Now the turntable turns the blank 3 axially by 90° on the basis of a programmed control. This produces an angular (see FIG. 2) resp. rounded (see FIG. 3) edge 15 resp. 15a.

After turning the blank 3 by 90°, the cutting equipment 4 again is moved on in the cutting direction x so that a closure surface 13 is created. At the end of the closure surface 13, the blank 3 is turned by a further 90° again with the formation of an angular edge 14, resp. 14a, so that now the S-shaped closure 10 is produced. Then the blank 3 is split along its entire length. With a precise guiding of the cutting equipment 4, exact symmetrical parts of a surgical instrument are obtained in spite of the closure. Now these parts may be further machined appropriately. Then the two parts are combined into the actual surgical instrument, in the present case a needle holder.

Figure 4:
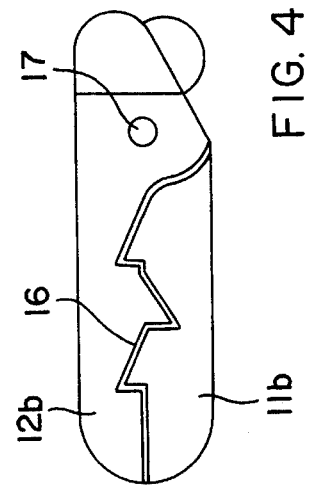
FIG. 4 shows a top view of jaw parts for, for example, endoscopic forceps.

The process invented may be used not only for producing entire two-part surgical instruments, but also, for example, symmetrically formed jaw parts, as is indicated in FIG. 4. In particular, FIG. 4 shows that between two jaw parts 11b and 12b the jaw surfaces may have any contour, for example toothing 16. This contour also is produced by the cutting equipment 4. The two jaw parts 11b and 12b are joined together by means of a hinge bolt 17.

I claim:

1. A process for producing a two part surgical instrument from a single blank comprising the steps of:

(a) mounting an elongated blank for rotational movement about a longitudinal axis A;

(b) mounting a cutting tool for axial movement along said axis A on a second longitudinal axis B substantially perpendicular to said axis A;

(c) moving said cutting tool a predetermined distance along said axis A for forming a first cut in said elongated blank of predetermined length;

(d) rotating said blank about said longitudinal axis A through a predetermined angle;

(e) further moving said cutting tool a further distance along said axis A for forming a second cut in said elongated blank of second predetermined length; and (f) repeating steps (d) and (e) to form the desired mirror image mating parts from said elongated blank.

2. A process according to claim 1 wherein said predetermined angle is about 90°.

3. A process according to claim 1 wherein said blank has an external surface and said process includes the step of final machining the external surface of the blank prior to forming the first cut.

4. A process according to claim 1 wherein said cutting tool is a wire erosion device.

* * * * *